Figure 1:
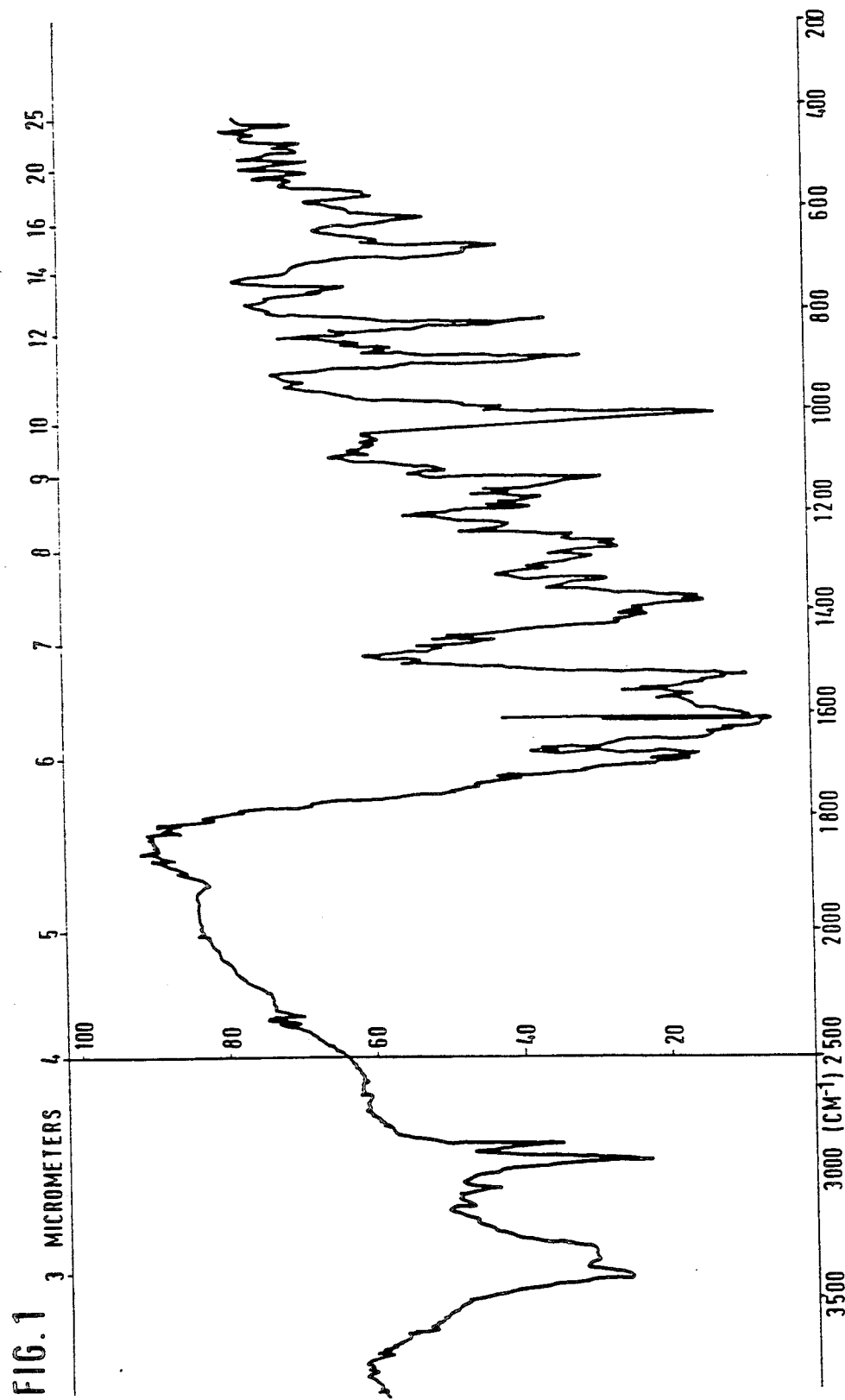

United States Patent [19]

Franco et al.

[11] Patent Number: 5,114,967
[45] Date of Patent: May 19, 1992

[54] ANTIBIOTIC ALISAMYCIN AND ITS USE

[75] Inventors: Christopher M. M. Franco; Erra K. S. Vijayakumar; Sugata Chatterjee; Bimal N. Ganguli; Jürgen Blumbach, all of Bombay, India; Herbert Kogler, Kelkheim; Hans-Wolfram Fehlhaber, Idstein/Taunus, both of Fed. Rep. of Germany

[73] Assignee: Hoechst Aktiengesellschaft, Frankfurt am Main, Fed. Rep. of Germany

[21] Appl. No.: 639,343

[22] Filed: Jan. 10, 1991

[30] Foreign Application Priority Data

Jan. 12, 1990 [EP] European Pat. Off. ........ 90100591.8

[51] Int. Cl.⁵ .................. A61K 31/335; C07D 303/14
[52] U.S. Cl. .................................... 514/475; 549/546
[58] Field of Search ......................... 549/546; 514/475

[56] References Cited

U.S. PATENT DOCUMENTS 4,595,770  6/1986  Brodasky et al. .................. 549/546

OTHER PUBLICATIONS

Grote et al., "Metabolic Products of Microorganisms, 244, Colabomycins, New Antibiotics of the Manumycin Group from *Streptomyces griseoflavus*", J. Antibiotics 41(9): 1178–1195 (1988).

Brodasky et al., "U-56, 407, A New Antibiotic Related to Asukamycin: Isolation and Characterization", J. Antibiotics 36(8): 950–956 (1983).

Slechta et al., "Isolation and Characterization of a New Antibiotic U-62162", J. Antibiotics 35(5): 556–560 (1982).

Zeeck et al., "The Structure of Manumycin", J. Antibiotics 40(11): 1530–1540 (1987).

Kakinuma et al., "The Structure of Asukamycin, a Possible Shunt Metabolite from 3-Dehydroquinic Acid in the Shikimate Pathway", J. Am. Chem. Soc. 101(12): 3402–3404 (1979).

Zeeck, A. et al., J. Antibiotics 41(11): 1541–1548 (1987).
Thiericke, R. et al., J. Antibiotics 41(11): 1549–1554 (1987).
Davis, B. D. et al., Microbiology, 3rd ed., pp. 583, 584, 621, 629, and 842 (1980).

*Primary Examiner*—C. Warren Ivy
*Assistant Examiner*—Amelia A. Owens
*Attorney, Agent, or Firm*—Finnegan, Henderson, Farabow, Garrett and Dunner

[57] ABSTRACT

Alisamycin, a compound of the formula I

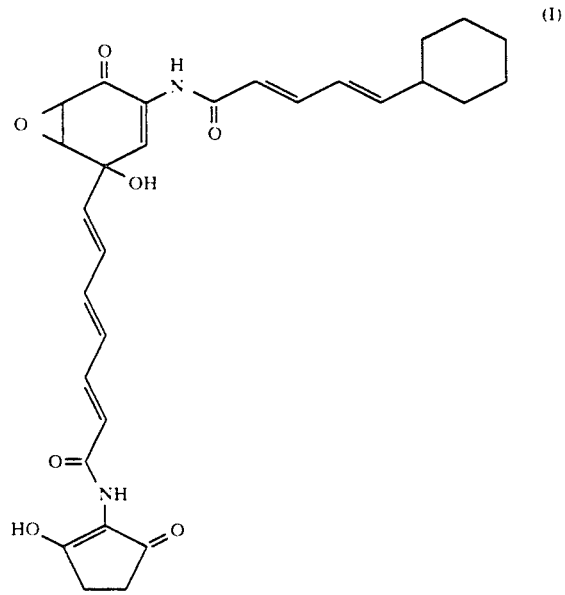

has an antibiotic, antitumor and antiparasitic action.

3 Claims, 3 Drawing Sheets

ANTIBIOTIC ALISAMYCIN AND ITS USE

The instant invention relates to a novel antibiotic, called Alisamycin, a process for its production with a new strain of microorganism, herein named Streptomyces species culture number HIL Y-88,31582 (Str. sp. Y-88,31582), its mutants and variants, its utilisation as a therapeutic drug.

Alisamycin is a compound of the formula I:

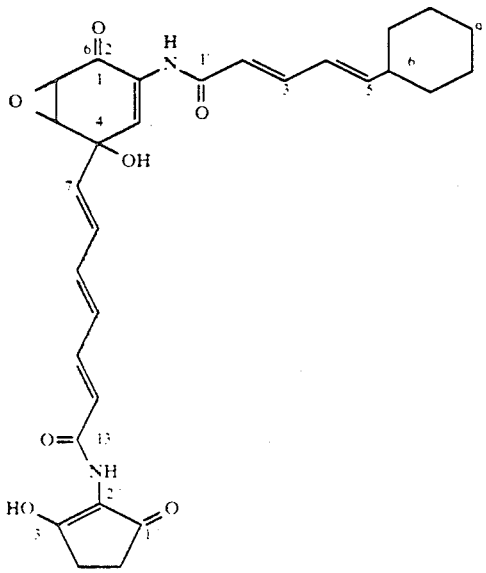

Str. sp. Y-88,31582 was isolated from soil collected at Alibag, Maharashtra, India. It has been deposited according to the conditions of the Treaty of Budapest with the Deutsche Sammlung von Mikroorganismen, Braunschweig at Oct. 4, 1989 (DSM No. 5559). Variants and mutants of culture number HIL Y-88,31582 can be obtained in a known manner using a mutagen, such as N-methyl-N-nitro-N'-nitrosoguanidine or ultraviolet light. The microorganism Str. sp. Y-88,31582 belongs to the order Actinomycetales, family Streptomycetaceae and genus Streptomyces.

Str. sp. Y-88,31582 is considered to be a new strain since it differs from the known strains in some of its morphological, cultural and physiological characteristics. It is considered to be a new strain also because it produces a new antibiotic compound herein called Alisamycin as will be clear from the description hereinafter.

As is apparent in the following detailed description of the invention, Alisamycin of this invention belongs to the Manumycin class of antibiotics, but differs from all known members of this class such as Manumycin (J. Antibiotics 40, 1530–1554, 1987), Asukamycin (J. Amer. Chem. Soc. 101, 3402–3404, 1979), Colabomycin (J. Antibiotics 41, 1178–1195, 1988), U-56407 (J. Antibiotics 36, 950–956, 1983) and U-62162 (J. Antibiotics 35, 556–560, 1982).

The novel antibiotic of this invention is active in vitro against a number of Gram-positive bacteria, yeasts and fungi. Accordingly, it may be used as a therapeutic drug in human and veterinary medicine; and in animal nutrition.

According to the present invention there is also provided a process for the isolation of Str. sp. Y-88,31582 from soil using a nutrient medium at a pH of 6.5 to 8.5 in known manner.

The nutrient medium used for isolation of the microorganism from soil consists of carbon and nitrogen sources, inorganic nutrient salts and solidifying agents. Sources of carbon may, for example, be glucose, starch, dextrin, glycerol, sucrose or molasses. Sources of nitrogen, for example, may be peptone, yeast extract, beef extract, malt extract casein or amino acids such as arginine or asparagine. The solidifying agent may, for example, be agar. The inorganic nutrient salts may, for example, be salts of sodium, potassium, magnesium, calcium, iron, zinc, manganese, copper, phosphorous or sulphur.

The microorganism of this invention elongates colourless aerial mycelia from branched substrate mycelia. Spores are formed in straight chains on top of aerial mycelia representative of Section Rectiflexiblis. Neither whirl or ascospores are observed. Mature spore chains contain more than 30 spores per chain. Based on the cultural and morphological characteristics of the microorganism on various agar media, as well as cell wall analysis which shows the presence of LL-diaminopimelic acid, we identify the producing organism as a Streptomyces sp.

It may be well understood to those skilled in the art that this invention is not limited to the particular organism which has been specified above but includes all those spontaneous and artificial mutants and variants derived from the said microorganism which are capable of producing the new antibiotic Alisamycin.

According to the present invention there is also provided a process for the production of Alisamycin, said process comprising cultivating Str. sp. Y-88,31582 by fermentation at a pH between 6.0 and 9.0, preferably between 6 and 7, and a temperature between 18°–40° C., preferably between 20 and 37 under aerobic conditions in a nutrient medium containing sources of carbon and nitrogen, nutrient inorganic salts, and trace elements, and isolating the compound from the culture broth in a known manner such as herein described.

The carbon sources used in the nutrient medium for production of the novel antibiotic may, for example, be glucose, starch, dextrin, glycerol, sucrose, molasses or oil. Sources of nitrogen used in the nutrient medium for production of the novel antibiotics may, for example, be soyabean meal, yeast extract, beef extract, malt extract, cornsteep liquor, peptone, gelatin or casein. Nutrient inorganic salts/mineral salts used in the nutrient medium, for production of the novel antibiotic may, for example, be sodium chloride, magnesium sulphate, ammonium sulphate or calcium carbonate. As trace elements, for instance iron, manganese, copper, zinc or cobalt may be used.

Preferably Str. sp. Y-88,31582 is cultivated at about 27° C. and pH about 7.0. The fermentation is preferably stopped after 23–48 hours when maximum yields of the compounds are obtained. The fermentation may, preferably, be submerged fermentation. The process of fermentation and formation of the novel antibiotic can be monitored by the antibacterial activity of the culture fluid and mycelium against Staphylococcus aureus 209 P in agar medium and by thin layer chromatography on silica gel plates with ethyl acetate as developing solvent.

If desired, an antifoaming agent such as Desmophen ® (a linear polyether based on propylene oxide Bayer AG. Leverkusen) may be used in the nutrient medium during fermentation of the culture.

Alisamycin can be obtained from the culture broth for example by extraction with a water-immiscible solvent after the pH has been adjusted to 6.5-7.5. The solvents could be ethyl acetate or chloroform; preferably, it is ethyl acetate and the preferred pH is 7.0. The solvent extract is concentrated to remove the solvent and then chromatographed further. Alisamycin can also be obtained from the culture broth by direct adsorption on suitable adsorbents such as Amberlite ® XAD-4 or 7 (porous adsorbent resin based on polystyrene or acrylic acid esters-Rohm and Haas Co., U.S.A.), or Diaion ® HP-20 (high porosity adsorbent resin based on a polystyrene divinylbenzene polymer, Mitsubishi Chemical Industries, Japan); the preferred adsorbent being Diaion ® HP-20. The compound according to the invention is eluted from the adsorbent using appropriate mobile phases, such as methanol or acetone, either singly, in combination with each other, or with water, and the eluates are then evaporated to dryness. The preferred eluant is methanol. The active eluates thus obtained are pooled and concentrated.

The aforementioned concentrated eluates or extracts containing Alisamycin, can be further purified in a number of ways. For example, re-adsorption and elution processes with activated carbon, Amberlite ® XAD-4 and 7, Diaion ® HP-20; gel filtration with Sephadex ® LH-20 gel (Pharmacia Fine Chemicals AB, Sweden) and its equivalents; adsorption chromatography on alumina and silica gel, can be conveniently combined for further purification. In addition, thin-layer chromatography, medium-pressure and high-pressure liquid chromatography using suitable adsorbents such as silica gel and modified silica gel-$C_{18}$ with suitable solvent systems may be used. Furthermore, counter current chromatography with a particular biphasic solvent system may work well for the said purpose. Preferably, silica gel chromatography with ethyl acetate and chloroform as the eluting solvents is used. Another purification process used either alone, or in combination with the abovementioned purification procedures, is based on the differential solubility of Alisamycin in organic solvents. The aforementioned concentrated extracts or eluates containing Alisamycin may be precipitated with hexane, repeatedly, in known manner. Alisamycin may also be precipitated from methanol:water (99:1) to remove impurities. Finally, Alisamycin may be crystallized in a suitable solvent, or mixture of solvents. The preferred solvent is acetonitrile.

Alisamycin is a pale yellow, crystalline powder. It is poorly soluble in water, methanol, ethanol, hexane and petroleum ether. It is fairly soluble in acetonitrile, methylene chloride, ethyl acetate and chloroform. It is very soluble in propylene glycol and dimethylsulfoxide.

The compound melts at temperature higher than 250° C. with decomposition.

In the thin layer chromatography (TLC) systems indicated below, Alisamycin has the following RF values:

TLC plate: Precoated silica gel plate: Article No. 5554 from E. Merck, Darmstadt.

| Rf of | EtOAc | CHCl$_3$:MeOH |
|---|---|---|
| Alisamycin | 0.51 | 0.44 |

In the analytical high-pressure liquid chromatography (HPLC) carried out using the conditions mentioned below, the $R_T = 3.5$ min.

Column packing: ODS-Hypersil ®-10 u.4x(30+100) mm

Flow Rate: 1.0 ml/min

Detection: 220 nm

Solvent: $CH_3CN$:0.1% Trifluoroacetic acid in water (55:45)

Spectroscopic data of Alisamycin

Figure 2:
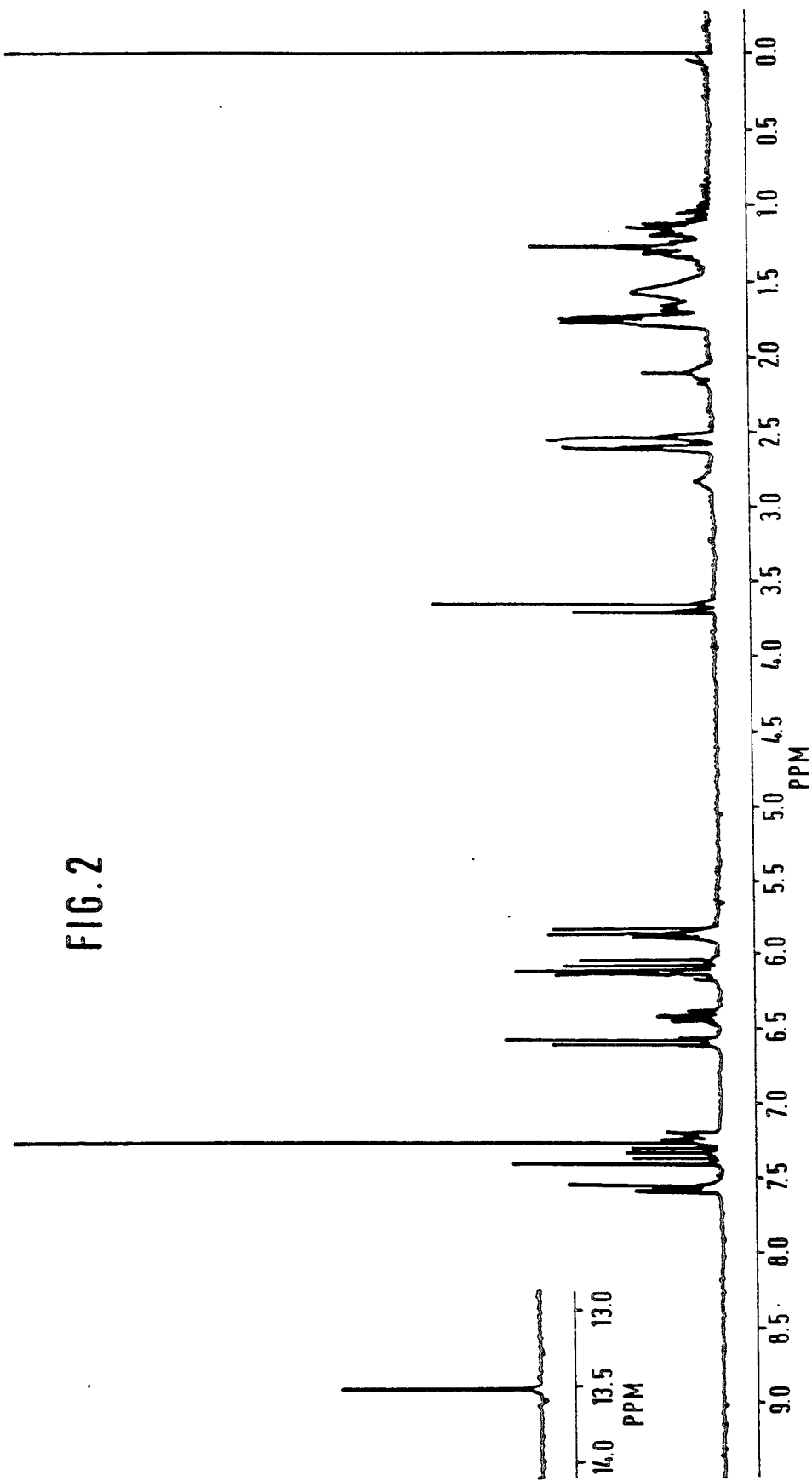
Figure 3:
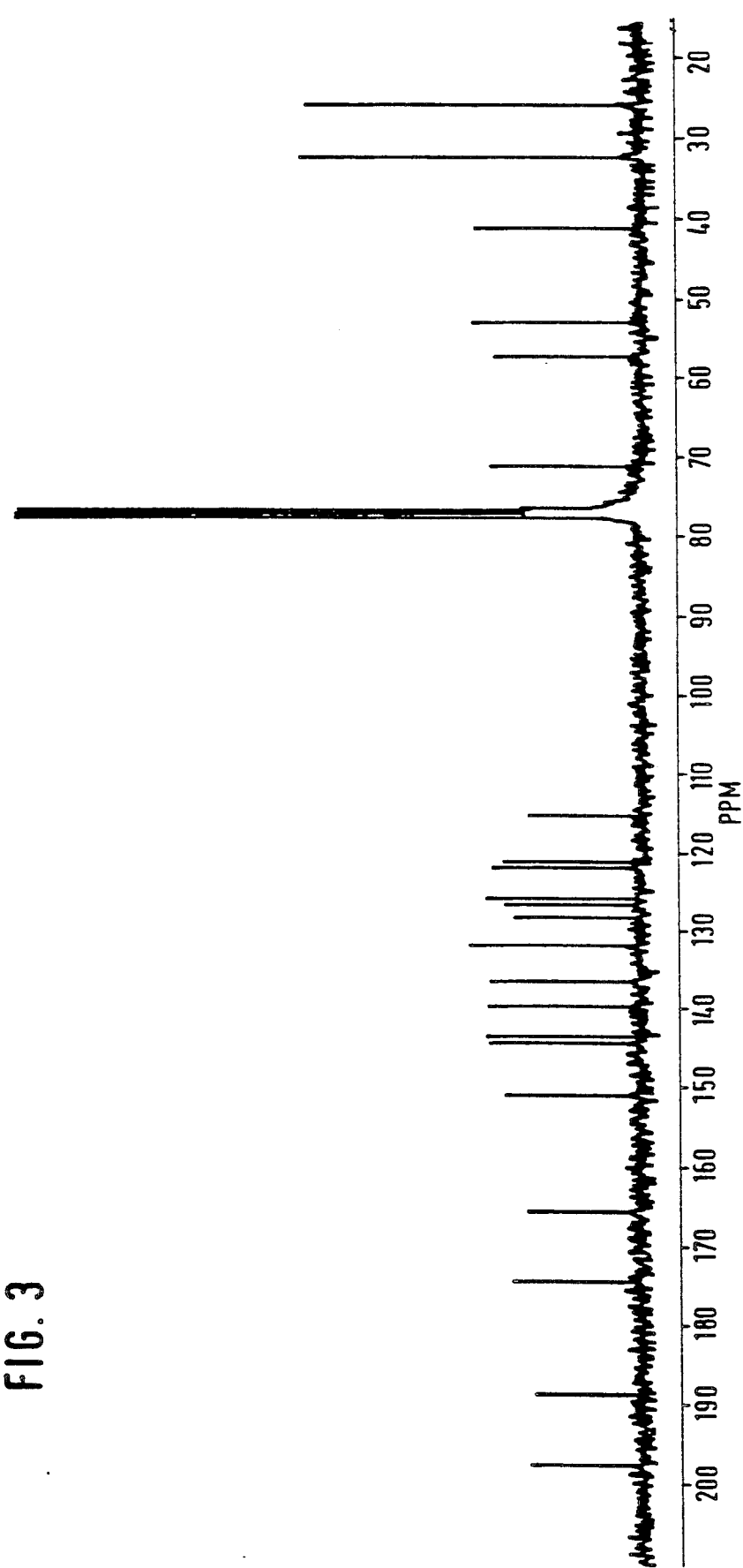

1. UV ($CH_3OH$): $\lambda_{max} = 276$ nm (log $\epsilon = 4.67$) and 316 nm (log $\epsilon = 4.57$)
2. IR (KBr): see FIG. 1
3. $^1$H-NMR (400 MHz, CDCl$_3$): Table A and FIG. 2
4. $^{13}$C-NMR (67.5 MHz, CDCl$_3$): Table B and FIG. 3
5. Molecular formula: $C_{29}H_{32}N_2O_7$ confirmed by high-resolution FAB mass spectrometry (matrix 3-nitrobenzylalcohol, reference polyethyleneglycol): $M+H^+$ ion measured m/z 521.228, calculated 521.229 for $^{12}C_{29}{}^1H_{33}{}^{14}N_2{}^{16}O_7$.

TABLE A $^1$H-NMR Signals of Alisamycin
(400 MHz, CDCl$_3$, 30° C.; chemical shifts in ppm relative to TMS = 0)

| Chem. shift | Multiplicity (couplings in Hz) | Structural assignment |
|---|---|---|
| 1.13 (2H) | m | 7'-$H_{ax}$ + 11'-$H_{ax}$ |
| 1.18 | m | 9'-$H_{ax}$ |
| 1.28 (2H) | m | 8'-$H_{ax}$ + 10'-$H_{ax}$ |
| 1.67 | m | 9'-$H_{eq}$ |
| 1.73 (2H) | m | 8'-$H_{eq}$ + 10'-$H_{eq}$ |
| 1.76 (2H) | m | 7'-$H_{eq}$ + 11'-$H_{eq}$ |
| 2.10 | m | 6'-$H_{ax}$ |
| 2.53 (2H) | m | 5''-$H_2$ |
| 2.61 (2H) | m | 4''-$H_2$ |
| 2.83 | br | 4-OH |
| 3.65 | d (3.6) | 6-H |
| 3.70 | dd (2.6 + 3.6) | 5-H |
| 5.84 | d (14.8) | 2'-H |
| 5.86 | dd (14.5 + 0.3) | 7-H |
| 6.05 | d (14.7) | 12-H |
| 6.12 | m | 5'-H |
| 6.12 | dd (10.5 + 15.5) | 4'-H |
| 6.42 | ddd (11.2 + 14.8 + 0.3) | 10-H |
| 6.58 | dd (11.3 + 14.5) | 8-H |
| 6.58 | dd (14.8 + 11.3) | 9-H |
| 7.22 | ddm (14.8 + 10.5) | 3'-H |
| 7.32 | dd (11.2 + 14.7) | 11-H |
| 7.40 | d (2.6) | 3-H |
| 7.54 | s | NH |
| 7.58 | s | NH |
| 13.52 | s | 3''-OH |

TABLE B $^{13}$H-NMR Signals of Alisamycin
(67.5 MHz, CDCl$_3$, 30° C.; chemical shifts in ppm relative to TMS the $^{13}$CDCl$_3$ signal = 77.0 ppm)

| Chem. shift | Multiplicity | Structural assignment |
|---|---|---|
| 25.65 | t | C-4'' |
| 25.80 (2C) | t | C-8' + C-10' |
| 26.00 | t | C-9' |
| 32.14 | t | C-5'' |
| 32.25 (2C) | t | C-7' + C-11' |
| 41.13 | d | C-6' |
| 52.93 | d | C-5 |
| 57.41 | d | C-6 |
| 71.20 | s | C-4 |
| 115.01 | s | C-2'' |
| 120.95 | d | C-4', C-5' |
| 121.59 | d | |

TABLE B-continued $^{13}$H-NMR Signals of Alisamycin
(67.5 MHz, CDCl$_3$, 30° C.; chemical shifts in ppm
relative to TMS the $^{13}$CDCl$_3$ signal = 77.0 ppm)

| Chem. shift | Multiplicity | Structural assignment |
|---|---|---|
| 125.52 | d | C-9, C-10 |
| 126.36 | d | |
| 128.08 | s | C-2 |
| 131.58 | d | C-2', C-12 |
| 131.74 | d | |
| 136.29 | d | C-8 |
| 139.52 | d | C-7 |
| 143.45 | d | C-3', C-11 |
| 144.16 | d | |
| 150.76 | d | C-3 |
| 165.16 | s | C-1', C-13 |
| 165.48 | s | |
| 174.15 | s | C-3" |
| 188.63 | s | C-1" |
| 197.39 | s | C-1 |

Alisamycin is active against gram-positive and gram-negative bacteria. When tested by the agar-well method in Antibiotic Assay medium and by the agar-dilution method in Mueller-Hinton agar (MIC) it has an activity which is shown in Table I below:

TABLE I

| | Zone diam (mm) | | MIC |
| Test Organism | 500 μg/ml | 32 μg/ml | (μg/ml) |
|---|---|---|---|
| 1. Staphylococcus aureus 209 p | 26 | 18.5 | 1.6 |
| 2. Staphylococcus aureus 20424 | 25 | 19 | 3.2 |
| 3. Staphylococcus aureus E88 | 27 | 14 | 6.4 |
| 4. Streptococcus faecalis UD56 | 16 | 13 | >50 |
| 5. Streptococcus faecalis Eder | 23 | 16 | 6.4 |
| 6. Streptococcus faecalis 23241 | 22 | 13 | 6.4 |
| 7. Escherichia coli 9632 | — | — | >50 |
| 8. Candida albicans | 10 | — | 50 |
| 9. Piricularia oryzae | 15 | 11 | >50 |
| 10. Botrytis cinerea 47 | 20 | — | >50 |

In addition to the antibacterial activity Alisamycin was also found to have antitumor and antiparasitic activities.

The invention will be further illustrated by preferred examples, but should not be considered as limited by those examples.

EXAMPLE I

Isolation of Streptomyces sp. Y-88,31582 from soil

| (a) Preparation of nutrient isolation media | | |
|---|---|---|
| Medium 1: | Glucose | 1.0 g |
| | Glycerol | 1.0 g |
| | L-arginine | 0.3 g |
| | K$_2$HPO$_4$ | 0.3 g |
| | MgSO$_4$.7H$_2$O | 0.2 g |
| | NaCl | 0.3 g |
| | Yeast extract | 2.0 g |
| | FeSO$_4$.7H$_2$O | 10.0 mg |
| | CuSO$_4$.5H$_2$O | 1 mg |
| | ZnSO$_4$.7H$_2$O | 1 mg |
| | MnSO$_4$.7H$_2$O | 1 mg |
| | Agar | 15.0 g |
| | Distilled water | 1 liter |
| | pH | 6.5 |
| Medium 2: | Glucose | 2.0 g |
| | L-asparagine | 1.0 g |

-continued

| (a) Preparation of nutrient isolation media | | |
|---|---|---|
| | K$_2$HPO$_4$ | 0.5 g |
| | MgSO$_4$.7H$_2$O | 0.5 g |
| | Soil Extract | 200 ml |
| | Agar | 15.0 g |
| | Distilled water | 800 ml |
| | pH | 8.0 |
| Medium 3: | Starch | 10.0 g |
| | Casein | 0.3 g |
| | KNO$_3$ | 2.0 g |
| | NaCl | 2.0 g |
| | K$_2$HPO$_4$ | 2.0 g |
| | MgSO$_4$.7H$_2$O | 0.05 g |
| | CaCO$_3$ | 0.02 g |
| | FeSO$_4$.7H$_2$O | 0.01 g |
| | Agar | 15.0 g |
| | Distilled water | 1 liter |
| | pH | 7.2-7.5 |

The media were sterilised at 121° C. for 30 minutes. In all cases, the sterilized media were cooled to 45° C., poured into petri plates and allowed to solidify.

(b) Preparation of soil suspension

One gram of soil was suspended in distilled water and shaken well. The soil was allowed to settle and the supernatent fluid was used to inoculate each one of the above-mentioned isolation media at a time.

(c) Inoculation of the isolation medium

One ml of the soil suspension was inoculated onto petri dishes containing 50 ml of any of the above mentioned nutrient isolation media.

(d) Isolation of Streptomyces sp. Y-88,31582

The inoculated petri dish was incubated at 30° C. for 10 days and Streptomyces sp. Y-88,31582 isolated from among the growing microorganisms.

EXAMPLE II

Cultivation of Streptomyces sp. Y-88,31582 for the fermentative production of Alisamycin S.treptomyces sp. Y-88,31582 was maintained on yeast extract-malt extract having the following composition:

| Malt extract | 10.0 g |
|---|---|
| Yeast extract | 4.0 g |
| Glucose | 4.0 g |
| Agar | 15.0 g |
| Distilled water | 1 liter |
| pH | 7.0 |

The medium was distributed in test tubes and sterilized at 121° C. for 30 minutes. The tubes were cooled in a slanting position for preparation of agar slants. The slants were inoculated with the culture and incubated at 28° C for 10-15 days when good growth and sporulation were observed. A suspension of the spores in distilled water from one slant was used to inoculate five 500 ml Erlenmeyer flasks each containing 100 ml of the seed culture medium.

Composition of the seed culture medium

| Glucose | 15.0 g |
|---|---|
| Soyabean meal | 15.0 g |
| Cornsteep liquor | 5.0 g |
| CaCO$_3$ | 2.0 g |

|  |  |
|---|---|
| NaCl | 5.0 g |
| Distilled water | 1 liter |
| pH | 6.5 |

The above medium was distributed in 100 ml amounts in 500 ml Erlenmeyer flasks and sterilized at 121° C. for 30 minutes. The flasks were cooled, inoculated with spore suspension or mycelial plugs and shaken at 240 r.p.m. for 72 hours at 27° (±1° C.) on a rotary shaker with 1.5 inch throw. The resultant growth was used to inoculate two hundred 500 ml flasks each containing 100 ml of the production culture medium at 2-4% (v/v).

Composition of the production medium

|  |  |
|---|---|
| Sucrose | 20.0 g |
| CaCO$_3$ | 2.5 g |
| KNO$_3$ | 1.0 g |
| K$_2$HPO$_4$ | 0.5 g |
| MgSO$_4$.7H$_2$O | 0.5 g |
| NaCl | 0.5 g |
| Distilled water | 1 liter |
| pH | 7.0 |

The fermentation was carried out at 27° C. (±1° C.) on a rotary shaker at 240 rpm with a 1.5 inch throw. When fermentation was discontinued at the end of 40-44 hours, the diameter of the zone of inhibition versus Staphyloccus aureus 209 P was 20 mm. when the culture filtrate was tested by the agar well (6 mm diameter) method and the pH of the culture fluid ranged from 7.1-7.30. The packed cell volume was 20% (v/v). The harvested culture broth containing the antibiotic was centrifuged to separate the mycelium and the culture fluid and further processed as described in Example IV.

EXAMPLE III

Cultivation of Streptomyces sp. YY-88,31582 for the fermentative production of Alisamycin The procedure of Example II was repeated with the following differences:

Str. sp. Y-88,31582 was grown on an agar medium with the following composition:

|  |  |
|---|---|
| Starch (soluble) | 10.0 g |
| K$_2$HPO$_4$ | 1.0 g |
| MgSO$_4$.7H$_2$O | 1.0 g |
| NaCl | 1.0 g |
| (NH$_4$)$_2$SO$_4$ | 2.0 g |
| CaCO$_3$ | 2.0 g |
| FeSO$_4$.7H$_2$O | 0.1 mg |
| MnCl$_2$.4H$_2$O | 0.1 mg |
| ZnSO$_4$.7H$_2$O | 0.1 mg |
| Agar | 15.0 g |
| Distilled water | 1 liter |
| pH | 7.2 |

The composition of the seed culture medium and production medium is similar to that in Example II.

2 ml of Desmophen ® was added as antifoam agent. 10 L of the production medium were taken in a 15 L fermenter. The medium was sterilized through direct and indirect steam for 20 minutes at 121° C. The fermenter was cooled and inoculated with seed culture (9% v/v). The fermentation was carried out at 27° C. (±1° C.) under stirred conditions at 150 r.p.m. with aeration at a rate of 10 litres per minute. When fermentation was discontinued at the end of 23-27 hours the pH of the culture broth was pH 7.3 and the diameter of the zone of inhibition versus (Staphylococcus aureus 209 P was 21 mm when the culture filtrate was tested by the agar well method (6 mm diameter). The packed cell volume was 15% (v/v). The culture broth was processed as in Example V.

EXAMPLE IV

Isolation and purification of Alisamycin

Approximately 16 litres of the culture filtrate, as obtained from Example II, was extracted twice with 10 litres each of ethyl acetate after adjusting the pH to 7.0. The aqueous layers were discarded and the combined ethyl acetate extracts were evaporated under vacuum to dryness.

This crude extract was dissolved in a minimum amount of ethyl acetate and precipitated with hexane. The procedure was repeated twice to obtain a dry powder (0.5 g). This powder was redissolved in a minimum amount of ethyl acetate to which ca. 50 ml methanol was added. Approximately 0.5 ml double distilled water was added and the solution was left for 16 hours at −20° C. The resultant precipitate was dissolved in acetonitrile; the acetonitrile solution was concentrated to saturation and then kept at −20° C. for over 48 hours. 150 mg pure crystalline Alisamycin was thus obtained.

EXAMPLE V

Isolation and purification of Alisamycin

Culture filtrates from two fermentor batches, as outlined in Example III, were pooled to give a volume of 17 litres. This was extracted twice with 10 litres each of ethyl acetate at pH 7.0. The ethyl acetate extract was concentrated to dryness to give 4.5 g crude compound. This crude compound was dissolved in a minimum amount of ethyl acetate and precipitated with hexane. This procedure was repeated thrice to obtain a dry powder (1.2 g) which was charged onto a 8×15 cm. glass column packed with 400 g silica gel (100-200 mesh) column. Alisamycin eluted out with a chloroform: ethyl acetate (70:30) to (65:35) gradient. The active eluates (1.5 L) containing Alisamycin were concentrated to dryness (0.42 g) and then dissolved in a minimum amount of ethyl acetate to which approximately 50 ml methanol was added. Approximately 0.5 ml double distilled water was added to this methanolic solution and the solution kept at −20° C. for a minimum of 16 hours. The resultant precipitate was dissolved in a minimum amount of ethyl acetate and then 50 ml acetonitrile. The acetonitrile solution was kept at −20° C. for a minimum of 48 hours. 110 mg pure yellow crystalline Alisamycin was thus obtained.

We claim:

1. Alisamycin, a compound of the formula

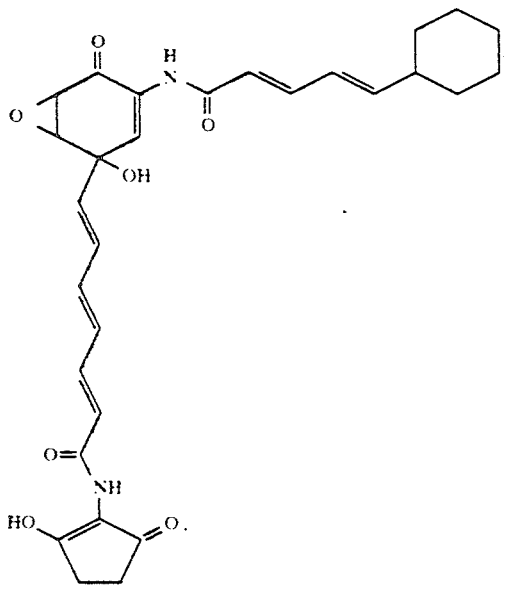
2. A pharmaceutical composition comprising an antibiotically effective amount of a compound as claimed in claim 1, together with a pharmacologically acceptable carrier.
3. A method of treating a mammal in need of an antibiotic treatment which comprises administering to said mammal an amount of a compound of claim 1 effective for said treatment.
* * * * *